United States Patent [19]

Hengge et al.

[11] Patent Number: 5,538,618
[45] Date of Patent: Jul. 23, 1996

[54] PROCESS FOR THE ELECTROCHEMICAL SYNTHESIS OF ORGANOSILICON COMPOUNDS, AND AN APPLIANCE FOR CARRYING OUT THE PROCESS, AND USE THEREOF FOR PREPARING ORGANOSILICON COMPOUNDS

[75] Inventors: Edwin Hengge, Graz-Andritz; Christa Jammegg, Graz, both of Austria; Wilfried Kalchauer, Burghausen, Germany

[73] Assignee: Wacker-Chemie GmbH, Munich, Germany

[21] Appl. No.: 260,841

[22] Filed: Jun. 16, 1994

[30] Foreign Application Priority Data

Jun. 17, 1993 [DE] Germany ............... 43 20 042.7

[51] Int. Cl.⁶ ..................................... C25B 3/00
[52] U.S. Cl. ................. 205/420; 204/257; 204/265; 204/277; 204/208; 204/290 R; 204/294
[58] Field of Search .................... 204/59 R, 72, 204/280, 290 R, 294, 246, 257, 265, 277

[56] References Cited

U.S. PATENT DOCUMENTS

| | | | |
|---|---|---|---|
| 3,103,473 | 9/1963 | Juda | 204/290 R |
| 4,292,434 | 9/1981 | Lindner et al. | 556/479 |
| 4,695,441 | 9/1987 | Lahoda et al. | 423/347 |

FOREIGN PATENT DOCUMENTS

| | | |
|---|---|---|
| 0032377 | 7/1981 | European Pat. Off. . |
| 0446578 | 9/1991 | European Pat. Off. . |
| 4024600 | 3/1991 | Germany . |
| 2234511 | 2/1991 | United Kingdom . |

OTHER PUBLICATIONS

"Electrosynthese en chimie organosilicique: Preparation de phenyl–et benzyl–trimethylsilanes", P. Pons et al., J. of Org. Chem., 321 (no month 1987) C27–C29.

"Electrosynthese en chimie organosilicique: Silylation selective de polychloromethanes", P. Pons et al., of Org. Chem., 358(no month 1988) 31–37.

Electrochimica Acta, Bd. 35, No. 11, (no month 1990), Oxford, UK, pp. 1867–1872 "Electroreductive Polymerisation of Organodichl oromonosilanes" by Umezawa et al.

Primary Examiner—John Niebling
Assistant Examiner—Edna Wang
Attorney, Agent, or Firm—Martin Connaughton

[57] ABSTRACT

A process is described for the electrochemical preparation of organosilicon compounds having at least one SiC-bound organic radical, a solution which contains at least one halosilane being subjected to an electrochemical reaction, an anode which contains a noble metal or an alloy consisting essentially of one or more noble metals having a halogen scavenger flowing around said anode.

8 Claims, No Drawings

PROCESS FOR THE ELECTROCHEMICAL SYNTHESIS OF ORGANOSILICON COMPOUNDS, AND AN APPLIANCE FOR CARRYING OUT THE PROCESS, AND USE THEREOF FOR PREPARING ORGANOSILICON COMPOUNDS

FIELD OF INVENTION

The present invention relates to a process for the electrochemical preparation of organosilicon compounds, and to an appliance for carrying out the process, and to the use of said appliance for preparing organosilicon compounds.

BACKGROUND OF INVENTION

Processes for the electrochemical synthesis of organosilicon compounds are already known. For example, EP-A2 446 578 describes a process for the electrochemical preparation of polysilanes from halomonosilanes. DE-A1 40 24 600 discloses an electrochemical process for the preparation of carbosilanes and polycarbosilanes from (haloalkyl)halosilanes. P. Pons et al., describe, in J. Organomet. Chem. 358 (1988), 31, and in J. Organomet. Chem. 321 (1987), C27, an electrochemical process for forming Si-C bonds by reacting chlorosilanes with organohalogen compounds.

All these electrochemical processes have in common that during the electrochemical process undesirable by-products are formed which either adversely affect the course of the reaction or are difficult to dispose of. If, as described in DE-A1 4024600, an inert anode is used in the electrochemical process, when an electrode of this type is employed, the elemental halogen is formed on the anode side. In the case described there, elemental chlorine is formed. This may react with the supporting electrolyte, the solvent and/or the silane used. This reaction has the effect that the solvent is chlorinated (halogenated) and reacts with the silane, or that a carbanion/radical is formed at the cathode and reacts with the silane. Alternatively, it is possible for the supporting electrolyte to have a lower solubility in the chlorinated (halogenated)solvent, some of it precipitating, as a result of which the current flow in the electrolytic cell is reduced. A further possibility is that of the anode being passivated by the halogen, as a result of which the current flow in the electrolytic cell is reduced.

If the anode is a non-inert anode (sacrificial anode), the formation of elemental halogen is indeed prevented. However, metal halides are formed in the process which must be worked up and disposed of in an appropriate manner. If the metal halides are soluble in the system and are not adequately complexed, they may migrate to the cathode and there react instead of the halosilane, i.e., the current yield is reduced drastically.

SUMMARY OF INVENTION

The object of the present invention is to prevent the formation of these undesirable by-products. This object is achieved by the present invention.

The invention relates to a process for the electrochemical preparation of organosilicon compounds having at least one SiC-bound organic radical, which comprises subjecting a solution which contains at least one halosilane to an electrochemical reaction, an anode which contains a noble metal or an alloy containing one or more noble metals having a halogen scavenger flowing around said anode.

The present invention further relates to an electrolytic appliance for carrying out the process according to the invention, in which there are arranged a cathode and an anode which contains a noble metal or an alloy containing one or more noble metals, there being arranged, inside or outside the anode, a guiding device for the halogen scavenger.

The invention also relates to the use of the electrolytic appliance for preparing organosilicon compounds.

The process according to the invention can be used in all known electrochemical processes for preparing organosilicon compounds. Preference is given, however, to the process in the preparation of organosilicon compounds which are a polysilane, disilane, cyclosilane or oligosilane. Particular preference is given to the process for the preparation of linear and/or cyclic organosilicon compounds, in which the linear compounds have 2 to 30 silyl units and the cyclic compounds have 3 to 6 silyl units.

Examples of the organic radicals which may be identical or different and which substitute the organosilicon compounds prepared according to the invention are alkyl and aryl radicals. In the case of the alkyl radicals, saturated hydrocarbon radicals having from 1 to 12 carbon atoms are preferred.

Examples of alkyl radicals are the methyl, ethyl, n-propyl, isopropyl, n-butyl, isobutyl, t-butyl, n-pentyl, isopentyl, neopentyl, t-pentyl radical; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical and cycloalkyl radicals such as cyclopentyl, cyclohexyl, cycloheptyl radicals and methylcyclohexyl radicals.

Particularly preferably, the alkyl radical is the methyl and the ethyl radical, especially the methyl radical.

Examples of aryl radicals are the phenyl and the naphthyl radical and alkaryl radicals such as o-, m-, p-tolyl radicals, xylyl radicals and ethylphenyl radicals, and aralkyl radicals such as the benzyl radical, the α- and the β-phenylethyl radical. The aryl radical is preferably the phenyl and the naphthyl radical, particularly preferably the phenyl radical.

The organosilicon compounds prepared according to the invention can be used for all purposes for which it had previously been possible to use organosilicon compounds. Thus, for example, the organo-polysilanes prepared according to the invention can be employed in processes for preparing silicon carbide (SIC) fibers. The hexamethyldisilane prepared according to the invention can be employed, e.g., as a starting compound for a trimethylsilyl protective group in the preparation of pharmaceuticals.

The halosilanes, organohalogen compounds, supporting electrolyte and solvents used in the process according to the invention can be any of the compounds used hitherto in electrochemical processes for preparing organosilicon compounds, as described, for example, in DE-A1 40 24 600 and EP-A2 446 578, and as quoted by P. Pons et al., in J. Organomet. Chem. 358 (1988), 31 and in J. Organomet. Chem. 321 (1987), C27.

The halosilanes and organohalogen compounds used are preferably the corresponding bromine and chlorine compounds, particular preference being given to chlorine compounds.

Examples of the halosilanes, dihalosilanes, trihalosilanes, tetrahalosilanes or halocarbohalosilanes are trimethylchlorosilane, trimethylbromosilane, triethylchlorosilane, dimethylethylchlorosilane, dimethyl-t-butylchlorosilane, dimethylphenylchlorosilane, methyldiphenylchlorosilane, dimethyldichlorosilane, dimethyldibromosilane, ethylmethyldichlorosilane, methylphenyldichlorosilane, methyl-t-butyldichlorosilane, di-n-propyldichlorosilane, methyl-n-hexyldichlorosilane, methyl-p-biphenyldichlorosilane, methyltrichlorosilane, methyltribromosilane, ethyltrichlorosilane, propyltrichlorosilane, tetrachlorosilane, chloromethyldimethylchlorosilane, 3-chloropropyldimethylchlorosilane, 1,1,1,2-tetramethyl-phenylchlorodisilane, 1,1,1,2,2-pentamethylchlorodisilane, 1,1,2,2-tetramethyldichlorodisilane, 1,1,2-trimethyl-2-phenyldichlorodisilane or mixtures thereof. Particular preference is given to dimethyldichlorosilane and trimethylchlorosilane.

Examples of organohalogen compounds are chlorobenzene, bromobenzene, carbon tetrachloride, trichloroethane, dichloroethane and benzyl chloride.

The supporting electrolytes used are inert salts or mixtures thereof which do not react with the reaction components. Examples of supporting electrolytes are salts of the general formula $M^+Y^-$, where M, represents Li, Na, $NBu_4$, $NMe_4$, $NET_4$, and Y means, $ClO_4$, Cl, Br, I, $NO_3$, $BF_4$, $AsF_6$, $BPh_4$, $PF_6$, $AlCl_4$, $CF_3SO_3$ and SCN, where Bu, Me, Et and Ph, respectively, represent a butyl, methyl, ethyl or phenyl group. Examples of suitable electrolytes include tetraethylammonium tetrafluoroborate and tetrabutylammonium tetrafluoroborate.

The solvents used can be any aprotic solvents which do not react with the halosilane and which are themselves reduced only at a more negative potential than the halosilanes. Suitable solvents are all those in which the compounds used are at least partially soluble under operational conditions with respect to concentration and temperature. In a special embodiment, the halosilane employed may itself serve as the solvent. A relevant example is dimethyldichlorosilane.

Examples of suitable solvents are tetrahydrofurane, acetonitrile, -butyrolactone, dimethoxyethane with nitromethane, 1,3-dioxolane, liquid $SO_2$, tris(dioxa-3,6-heptyl)amine, trimethylurea, dimethyl formamide, dimethylsulfoxide, 1,2-dimethoxyethane, bis(2-methoxyethyl) ether, p-dioxane and hexamethylphosphoramide, and mixtures of these solvents.

The selection of the reaction conditions, such as the concentration of the individual components, the reaction temperature, which is preferably at room temperature, the reaction pressure, which is preferably atmospheric pressure, the cathode material comprised of conductive metals or alloys, such as, silver, platinum, steel or graphite, steel being preferred, and the current density are within the general expertise of those skilled in the art. Alternatively, it is possible, however, to employ higher or lower reaction temperatures and reaction pressures.

The process according to the invention can be carried out in any conventional way, using an electrolytic cell having a cathode and an anode. The electrolytic cell may be a divided or undivided electrolytic cell, the undivided electrolytic cell being preferred as it has the simplest configuration.

The process takes place under an inert gas atmosphere, with the options of using nitrogen, argon or helium as the inert gases. Preference is given to the use of nitrogen.

The electrolytic cell is provided with a potentiostat or a galvanostat in order to control the potential or the intensity of the current. The reaction can be carried out with and without a controlled potential.

The electrodes which can be used as the cathode are preferably made of graphite or an inert metal such as gold, silver, platinum or another metal or an alloy which is relatively inert, e.g., stainless steel, inert meaning that the cathode under the reaction conditions selected does not undergo chemical change.

The counterelectrode (anode) may be comprised of any materials which have adequate electric conductivity, are chemically inert under the reaction conditions selected and are coated with, or already consist of, a noble metal or an alloy containing one or more noble metals, the noble metals used being rhenium, ruthenium, rhodium, osmium, iridium, platinum or palladium, of which platinum and/or palladium or alloys containing platinum and/or palladium are preferred. In the case of a coated anode, the anode base material to be coated is preferably silicon carbide, iron silicide or graphite. Particular preference is given to graphite as the base material and to palladium and/or platinum or alloys containing platinum and/or palladium as the coating material, palladium being preferred as it is less expensive to procure.

A preferred coating of the base material of the anode is effected as follows: an aqueous palladium salt solution is applied to a graphite electrode, and after drying of the electrode the palladium is reduced to the metal. The coating on the anode need not be complete, i.e., provide a seal. A layer thickness of $\leq 0.2$ μm is sufficient. Alternatively, a layer thickness of more than 0.2 μm may be chosen, however. As the noble metal has a catalytic effect, catalytic amounts of the noble metal or the noble metal-containing alloy which are distributed over the surface are sufficient.

The coating may also be applied to the electrode by electrochemical deposition from solutions.

The halogen scavengers employed at the reaction temperature, preferably at room temperature, are gaseous unsaturated hydrocarbons such as, propene, butene, butadiene, ethene, ethyne or hydrogen. Alternatively, mixtures of various halogen scavengers may be employed. Preferably, halogen scavengers are used whose reaction products at the reaction temperature are gaseous and consequently are readily removed from the reaction system. A particularly preferred embodiment consists of using chlorides/chlorosilanes as the halogen compounds and hydrogen as the halogen scavenger.

The halogen scavenger is apportioned in such a way that the gas flows around the anode. This may be done by placing a gas conduit, through which the halogen scavenger is introduced into the system below the anode. In a particularly preferred embodiment, the anode used is a porous graphite tube coated with platinum or palladium or with alloys containing platinum and/or palladium. The anode is closed at the bottom end; at the top end, the halogen scavenger is introduced into the electrode with the aid of a metal tube which, at the same time, may serve as a current feed. The halogen scavenger is passed through the pores of the graphite tube to the external anode surface and there reacts with the halogen produced.

The amounts of halogen scavenger depends on the size of the equipment, the design of the anode and the design of the electrolytic cell and must be set in such a way that the anode during the electrolysis is completely surrounded by flowing halogen scavenger. Based on the electrochemical reaction, the halogen scavenger must be employed in stoichiometric excess.

If hydrogen is used as the halogen scavenger, the reaction product formed is the hydrogen halide; if ethene and ethyne are used as halogen scavengers, saturated halohydrocarbons are formed. The excess of halogen scavenger and the reaction products are continuously removed from the electrolytic system. Subsequent separation of halogen scavenger and reaction product may be effected, for example, by fractionated condensation or by scrubbing and adsorption processes. The halogen scavenger in excess can be reintroduced into the electrolytic cell.

The electrolytic appliance according to the invention is described with reference to a preferred embodiment. The electrolysis equipment used is a quick-fit vessel having a cylindrically symmetric electrode configuration (undivided cell). The anode is located in the center of the system and is a porous graphite tube coated with platinum or palladium or with alloys containing platinum and/or palladium. The anode is closed at the bottom end, open at the top end, the open top end being connected, in a gastight and current-conducting manner, with a guiding device for the halogen scavenger. The guiding device is, for example, a gastight graphite tube or a metal tube, preferably a metal tube, the metal tube being able to serve as a current feed at the same time. Alternatively, however, the guiding device may be disposed below the anode in the form of a gas conduit, so that the halogen scavenger is introduced into the system through said conduit.

General procedure:

The supporting electrolytes used are dried, prior to the reaction, in an oil pump vacuum at 50° C. Tetrahydrofuran (THF) is dried by distillation over an Na/K alloy, hexamethylphosphoramide (HMPA) is freed of traces of moisture by the addition of NaH and subsequent distillation. The silanes used are purified by distillation prior to the reaction. All process steps are carried out under an inert gas atmosphere (nitrogen), the electrolyses being performed galvanostatically at room temperature.

Anode preparation:

The anodes used are platinized platinum electrodes (commercially available from Heraeus GmbH) or porous graphite anodes coated with palladium or platinum. A porous graphite rod (commercially available from SIGRI GmbH) is provided with an internal bore through which the hydrogen is introduced. The cleaned graphite anode has a solution applied to it, by brushing, which consists of 2 g of palladium(II) chloride (20 g of hexachloroplatinic acid), 20 ml of concentrated hydrochloric acid and 50 ml of water. After drying of the electrode, it has applied to it, in order to reduce the noble metal, a 37% strength formaldehyde solution. Then the electrode is washed with 30% strength aqueous sodium hydroxide and with water. Prior to being used, the anode is dried at 80° C. in an oil pump vacuum; then a metal tube is attached in a gastight manner to the open top end of the anode.

EXAMPLE 1

0.43 g of tetraethylammonium tetrafluoroborate is dissolved in a mixture of 50 ml of tetrahydrofuran and 50 ml of hexamethylphosphoramide and transferred into a dry electrolytic cell purged with inert gas. After the addition of 100 ml of dimethyldichlorosilane, a turbid solution is formed which is electrolyzed with the aid of a platinum-coated graphite anode at a constant current of 50 mA (current density 0.5 mA/cm$^2$). The hydrogen is introduced into the system via the porous anode at approximately 320 ml/h; the excess hydrogen and the hydrogen chloride formed are removed from the system via a gas washing bottle filled with silicone oil. In order to separate entrained chlorosilanes, the gas stream is cooled to −60° C. and then passed into 50 ml of 0.1N $AgNO_3$ solution. The amount of AgCl formed is determined after the reaction by potentiometric titration of the remaining amount of $AgNo_3$, using 0.1N KCl solution.

After a reaction time of 8 hours, the electrolysis is discontinued; the precipitate formed at the cathode is filtered off, washed with THF and dried in vacuo. The precipitate (0.18 g) can be identified, by means of IR spectroscopy, as dimethylpolysilane. The current yield, based on the amount of HCl detected (the amount of HCl remaining in the solution is not measured) is 21%.

EXAMPLE 2

0.3 g of tetrabutylammonium tetrafluoroborate is dissolved in 20 ml of HMPA and, together with 180 ml of $Me_2SiCl_2$, and introduced into the electrolytic cell. The procedure is then performed as described in Example 1. The electrolysis is carried out with 58 mA (current density 0.58 mA/cm$^2$). After 8 hours, 0.22 g of dimethylpolysilane is obtained; this corresponds to a current yield of 42%, based on the detected amount of HCl.

EXAMPLE 3

Analogous to Example 1, except that instead of dimethyldichlorosilane, 100 ml of trimethylchlorosilane are electrolyzed. Over a reaction time of 20 hours, 1.44 g of hexamethyldisilane are formed. The analysis of hexamethyldisilane is performed by means of $^{29}$Si-NMR spectroscopy (−19.7 ppm with respect to tetramethylsilane (TMS) standard) and by means of gas chromatography/mass spectroscopy (GS/MS) (molecular mass peak 146). The current yield, based on the hydrogen chloride, is 30%.

EXAMPLE 4

Analogous to Example 2, except that a graphite anode coated with palladium is used. The yield is 0.21 g of dimethylpolysilane, the current yield being determined as 39%.

EXAMPLE 5

Analogous to Example 2, except that a platinized platinum electrode is used and the hydrogen is introduced into the system with the aid of a gas injection tube below the anode. The reaction temperature is 40° C. The yield is 0.21 g of dimethylpolysilane, the current yield being determined as 42%.

What is claimed is:

1. A process for the electrochemical preparation of organosilicon compounds having at least one SiC-bound organic radical, which comprises subjecting a solution containing at least one halosilane, optionally organohalogen compounds, supporting electrolyte and optionally solvents to an electrochemical reaction in the presence of an anode comprised of one or more noble metals and equipped with a guiding device for directing a flow of a gaseous halogen scavenger around said anode.

2. The process as claimed in claim 1, wherein the halosilane is a chlorosilane.

3. The process as claimed in claim 1, wherein the organosilicon compounds are polysilanes, disilanes, cyclosilanes or oligosilanes.

4. The process as claimed in claim 1, wherein linear, cyclic or a mixture of linear and cyclic organosilicon compounds are prepared, the linear compounds having 2 to 30 silyl units and the cyclic compounds having 3 to 6 silyl units.

5. The process as claimed in claim 1, wherein the anode is a porous graphite tube having a top end and a bottom end and an interior wherein the tube is coated with a noble metal or an alloy containing one or more noble metals, is closed at the bottom end, open at the top end, and is provided with the guiding device for the halogen scavenger in its interior.

6. The process as claimed in claim 1, wherein the halogen scavenger is selected from the group consisting of ethene, ethyne, hydrogen or mixtures of these substances.

7. An electrolytic appliance for the electrochemical preparation of organosilicon compounds, comprising a cathode and an anode wherein the anode is coated with a noble metal or an alloy containing one or more noble metals, there being arranged, inside or outside the anode, a guiding device for directing the flow of a halogen scavenger wherein the guiding device also serves as a current feed.

8. The electrolytic appliance as claimed in claim 7, in which the anode is a porous graphite tube having a top end, a bottom end and an interior end which has a coating consisting essentially of platinum, palladium or alloys thereof, which tube is closed at the bottom end, open at the top end, and is provided with the guiding device for the halogen scavenger in its interior.

* * * * *